(12) United States Patent
Cleary et al.

(10) Patent No.: US 7,137,812 B2
(45) Date of Patent: Nov. 21, 2006

(54) APPARATUS FOR INDIRECT BONDING OF ORTHODONTIC APPLIANCES AND METHOD OF MAKING THE SAME

(75) Inventors: James D. Cleary, Glendora, CA (US); David K. Cinader, Yorba Linda, CA (US); Oliver L. Puttler, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 18 days.

(21) Appl. No.: 10/678,286

(22) Filed: Oct. 3, 2003

(65) Prior Publication Data

US 2005/0074716 A1    Apr. 7, 2005

(51) Int. Cl.
*A61C 7/00* (2006.01)
*B65D 81/30* (2006.01)

(52) U.S. Cl. .......................... 433/3; 206/63.5; 206/368
(58) Field of Classification Search .................. 433/6, 433/24, 2, 3, 9; 206/63.5, 368, 369
See application file for complete search history.

(56) References Cited

U.S. PATENT DOCUMENTS

| | | | |
|---|---|---|---|
| 4,501,554 A | 2/1985 | Hickham | |
| 4,523,908 A | 6/1985 | Drisaldi et al. | |
| 4,626,208 A | 12/1986 | Hall | |
| 4,657,508 A | 4/1987 | Dellinger | |
| 4,888,489 A | 12/1989 | Bryan | |
| 5,015,180 A | 5/1991 | Randklev | |
| 5,147,204 A | 9/1992 | Patten et al. | |
| 5,172,809 A | 12/1992 | Jacobs et al. | |
| 5,354,199 A | 10/1994 | Jacobs et al. | |
| 5,429,229 A | 7/1995 | Chester et al. | |
| 5,487,662 A | 1/1996 | Kipke et al. | |
| 5,538,129 A | 7/1996 | Chester et al. | |
| 5,634,711 A | 6/1997 | Kennedy et al. | |
| 5,702,250 A | 12/1997 | Kipke | |
| 5,711,665 A | 1/1998 | Adam et al. | |
| 5,863,198 A | 1/1999 | Doyle | |
| 5,971,754 A | 10/1999 | Sondhi et al. | |
| 6,050,815 A * | 4/2000 | Adam et al. | 433/9 |
| 6,082,995 A * | 7/2000 | Wise | 433/6 |
| 6,089,861 A | 7/2000 | Kelly et al. | |
| 6,123,544 A | 9/2000 | Cleary | |
| 6,126,443 A | 10/2000 | Burgio | |
| 6,142,780 A | 11/2000 | Burgio | |
| 6,302,688 B1 | 10/2001 | Jordan et al. | |

(Continued)

FOREIGN PATENT DOCUMENTS

JP    2000-14681    6/2000

(Continued)

OTHER PUBLICATIONS

Pending U.S. Appl. No. 10/428,301.

(Continued)

*Primary Examiner*—Cary E. O'Connor
(74) *Attorney, Agent, or Firm*—James D. Christoff (57) ABSTRACT

Apparatus for use in indirect bonding of orthodontic appliances includes a container having a chamber and a placement device received in the chamber. At least one orthodontic appliance is releasably connected to the placement device and has a base with a contour that is a replica of a portion of the patient's tooth structure. A bonding composition for bonding the appliance to the patient's tooth structure is applied to the base before the container is closed by the manufacturer, such that the practitioner can simply remove the placement device from the chamber and immediately transfer the appliances to the patient's teeth.

19 Claims, 5 Drawing Sheets

U.S. PATENT DOCUMENTS

| | | |
|---|---|---|
| 6,386,865 B1 | 5/2002 | Suh et al. |
| 6,419,483 B1 | 7/2002 | Adam et al. |
| 6,554,613 B1 | 4/2003 | Sachdeva et al. |
| 6,565,355 B1 | 5/2003 | Kim et al. |
| 6,607,382 B1 | 8/2003 | Kuo et al. |
| 6,705,863 B1 | 3/2004 | Phan et al. |
| 2002/0028417 A1 | 3/2002 | Chapouland et al. |
| 2003/0163291 A1 | 8/2003 | Jordan et al. |
| 2003/0196914 A1 | 10/2003 | Tzou et al. |
| 2003/0198914 A1 | 10/2003 | Brennan et al. |

FOREIGN PATENT DOCUMENTS

| | | |
|---|---|---|
| JP | 2002-102256 | 4/2002 |
| WO | WO 99/22667 | 5/1999 |
| WO | WO 02/089693 | 11/2002 |

OTHER PUBLICATIONS

Pending U.S. Appl. No. 60/494,603.

Pending U.S. Appl. No. 10/678,841, filed Oct. 3, 2003.

Pending U.S. Appl. No. 10/428,255, filed May 2, 2003.

Moskowitz et al., A New Look at Indirect Bonding, Journal of Clinical Orthodontics, 1996, vol. XXX No. 5, pp. 277-281.

Hickham, Predictable Indirect Bonding, Journal of Clinical Orthodontics, 1993, vol. XXVII, No. 4, pp. 215-217.

Sinha et al., A Thermal-Cured Fluoride-Releasing Indirect Bonding System, Journal of Clinical Orthodontics, 1995, vol. XXIX, No. 2, pp. 97-100.

Cooper et al., Indirect Bonding with Adhesive Precoated Brackets, Journal of Clinical Orthodontics, Mar. 1993, vol. XXVII, No. 3, pp. 164-167.

Reichheld et al., An Indirect Bonding Technique, Journal of Clinical Orthodontics, 1990, vol. XXIV, No. 1, pp. 21-24.

Kasrovi, A New Approach To Indirect Bonding Using Light-Cure Composites, American Journal of Orthodontics and Dentofacial Orthopedics, Jun. 1997, pp. 652-656.

* cited by examiner

APPARATUS FOR INDIRECT BONDING OF ORTHODONTIC APPLIANCES AND METHOD OF MAKING THE SAME

BACKGROUND OF THE INVENTION

1. Field of the Invention

This invention broadly relates to apparatus for bonding orthodontic appliances such as brackets to a patient's teeth. The invention also relates to methods for making apparatus for indirect bonding of orthodontic appliances. The present invention facilitates precise placement of the appliances in predetermined locations on the teeth and in selected orientations relative to the teeth, and also reduces the overall amount of time for the bonding procedure.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. Consequently, if a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

In general, orthodontic appliances that are adapted to be adhesively bonded to the patient's teeth are placed and connected to the teeth by either one of two techniques: a direct bonding technique, or an indirect bonding technique. In the direct bonding technique, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place.

While the direct bonding technique described above is in widespread use and is considered satisfactory by many, there are shortcomings that are inherent with this technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally dislodged from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some amount of time may be necessary before the practitioner is satisfied with the location of each appliance. At the same time, however, the patient may experience discomfort during the procedure and have difficulty in remaining relatively motionless, especially if the patient is an adolescent. As can be appreciated, there are aspects of the direct bonding technique that can be considered a nuisance for both the practitioner and for the patient.

Indirect bonding techniques avoid many of the problems noted above. In general, indirect bonding techniques known in the past have involved the use of a placement device having a shape that matches the configuration of at least part of the patient's dental arch. One type of placement device is often called a "transfer tray" and typically has a cavity for receiving a number of teeth simultaneously. A set of appliances such as brackets are releasably connected to the tray at certain, predetermined locations.

Other types of placement devices used in indirect bonding are often referred to as "jigs" and resemble a framework that contacts one or more teeth at certain locations. For example, a jig constructed for use in bonding a single appliance to a single tooth may have an arm that extends over and contacts an incisal section of the tooth. An appliance such as a bracket is releasably connected to the jig at a certain, predetermined location relative to the tooth.

During the use of orthodontic placement devices for indirect bonding, an adhesive is typically applied to the base of each appliance by the orthodontist or a staff member. The device is then placed over the patient's teeth and remains in place until such time as the adhesive hardens. Next, the device is detached from the teeth as well as from the appliances, with the result that all of the appliances previously connected to the device are now bonded to respective teeth at their intended, predetermined locations.

In more detail, one method of indirect bonding of orthodontic appliances using the transfer tray described above includes the steps of taking an impression of each of the patient's dental arches and then making a replica plaster or "stone" model from each impression. Next, the appliances are bonded to the stone models at desired locations. Optionally, the bonding adhesive can be a chemical curing adhesive (such as Concise brand adhesive from 3M) or a light-curable adhesive (such as Transbond XT brand adhesive or Transbond LR brand adhesive from 3M). Optionally, the brackets may be adhesive precoated brackets such as those described in U.S. Pat. Nos. 5,015,180, 5,172,809, 5,354,199 and 5,429,229.

The transfer tray is then made by placing a matrix material over the model as well as over the appliances placed in the model. For example, a plastic sheet matrix material may be held by a frame and exposed to radiant heat. Once the plastic sheet material has softened, it is placed over the model and the appliances. Air in the space between the sheet material and the model is then evacuated, and the plastic sheet material assumes a configuration that precisely matches the shape of the replica teeth of the stone model and attached appliances.

The plastic sheet matrix material is then allowed to cool and harden to form a tray. The tray and the appliances (which are embedded in an interior wall of the tray) are then detached from the stone model. If the cured adhesive that was used to bond the appliances to the stone model remains on the base of the appliances after detachment from the stone model, the adhesive serves as a "custom" base having a concave contour that precisely replicates the convex contour of the previous attachment location of the stone model, as well as the convex configuration of the intended mounting location of the appliances on the patient's teeth.

Once the patient has returned to the practitioner's office, a quantity of adhesive is placed on the base of each appliance, and the tray with the embedded appliances is then placed over the matching portions of the patient's dental arch. Since the configuration of the interior of the tray closely matches the respective portions of the patient's dental arch, each appliance is ultimately positioned on the patient's teeth at precisely the same location that corresponds to the previous location of the same appliance on the stone model.

Indirect bonding techniques offer a number of advantages over direct bonding techniques. For one thing, and as indicated above, it is possible to bond a plurality of appliances to a patient's dental arch simultaneously, thereby avoiding the need to bond each appliance in individual fashion. In addition, the placement device helps to locate the appliances in their proper, intended positions such that adjustment of each appliance on the surface of the tooth before bonding is avoided. The increased placement accuracy of the appliances that is often afforded by indirect bonding techniques helps ensure that the patient's teeth are moved to their proper, intended positions at the conclusion of treatment.

In recent years, many improvements have been made in the field of indirect bonding. For example, U.S. Pat. No. 5,971,754 describes a two-component indirect bonding adhesive with a relatively fast curing time that reduces the length of time that the tray must be firmly held against the patient's teeth. U.S. Pat. No. 6,123,544 describes a transfer tray that receives movable arms for placing appliances on the patient's teeth once the tray is positioned in the oral cavity. Pending U.S. patent application entitled "METHOD AND APPARATUS FOR INDIRECT BONDING OF ORTHODONTIC APPLIANCES" (U.S. Ser. No. 10/428, 301, filed May 2, 2003), describes among other things a transfer apparatus with an improved matrix material for releasably holding appliances in place.

Although the advancements described above in the field of indirect bonding are significant, there is a continuing need to further improve the state of the art so that the practitioner's time in completing the bonding procedure is reduced. Such a reduction in time may also serve to benefit the patient since the amount of chair time is reduced.

However, it is also important to ensure that the strength of the bond between the appliance and the tooth as a result of the indirect bonding technique is sufficiently high. If the bond strength is insufficient, there is an increased risk that the appliance will inadvertently detach from the tooth during the course of treatment. Detachment of appliances is considered a significant nuisance, because the course of treatment is then interrupted until such time as the patient returns to the practitioner for reattachment of the appliance or replacement of the appliance with a new appliance.

SUMMARY OF THE INVENTION

The present invention is directed to an improved indirect bonding apparatus wherein one or more orthodontic appliances are connected to a placement device. Each appliance has a base with a contour that is a replica of a contour of the patient's tooth structure. In addition, a bonding composition is provided on the base by the manufacturer, so that the need to apply a bonding composition in the practitioner's office may be avoided.

Preferably, the indirect bonding apparatus is received in a container having a chamber that serves to protect the bonding composition during shipping and storage. Once the container has been opened, the placement device can be immediately transferred to the patient's dental arch without delay. As a result, the need for the practitioner to prepare the base of each appliance for bonding is eliminated.

Moreover, the precise, mating fit between the pre-formed base of each appliance and its intended mounting location on the patient's tooth helps to increase the bond strength between the appliance and the tooth surface. This mating fit reduces the likelihood that small gaps or voids may be present between the appliance and the tooth surface and increases the likelihood that a layer of adhesive having a uniform thickness is present across the entire surface of the base of the appliance. As a consequence, the risk of unintentional detachment of the appliance from the tooth during the course of treatment is reduced. The elimination of gaps or voids between the appliance and the tooth surface also helps reduce the possibility that food particles and other debris may be retained in contact with the tooth enamel and cause the formation of caries.

In more detail, the present invention in one aspect relates to apparatus for use in indirect bonding of orthodontic appliances. The apparatus comprises a container having a chamber, and an orthodontic placement device received in the chamber. The placement device has a construction matching at least a portion of the patient's dental arch. At least one orthodontic appliance is releasably connected to the placement device and has a base with a contour that is a replica of the contour of a portion of the patient's tooth structure. Additionally, a bonding composition is provided on the base for bonding to the patient's tooth structure.

Another aspect of the present invention is directed to a method of making an apparatus for orthodontic indirect bonding. The method comprises:

providing at least one orthodontic appliance;

determining the contour of at least a portion of the patient's tooth structure;

forming a base on each appliance to match a portion of the patient's tooth structure;

connecting each appliance to a placement device;

applying a quantity of bonding composition to each base; and placing the placement device within a container.

Additional aspects of the present invention are described in the paragraphs that follow and are illustrated in the accompanying drawings.

DETAILED DESCRIPTION OF THE PREFERRED EMBODIMENTS

Figure 1:
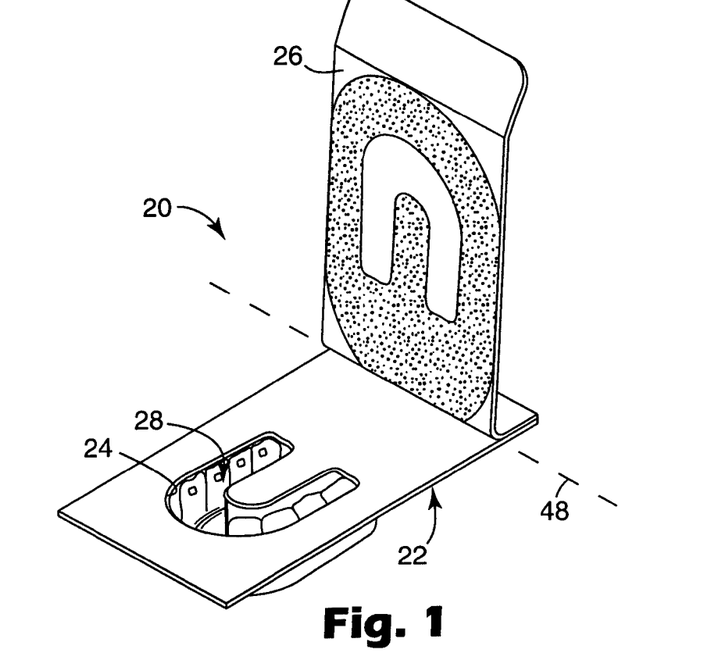
FIG. 1 is a perspective view showing an apparatus for use in indirect bonding of orthodontic appliances according to one embodiment of the present invention, wherein the apparatus includes a container and a placement device received in a chamber of the container.
Figure 2:
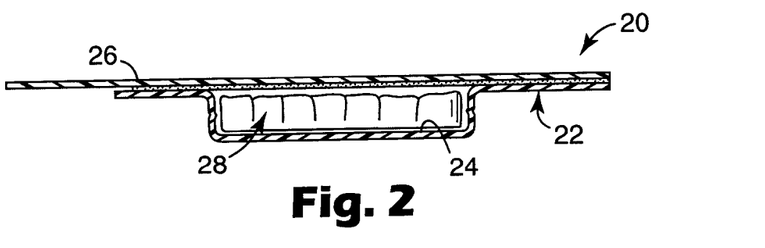
FIG. 2 is a side cross-sectional view of the apparatus shown in FIG. 1, except that a cover of the container has been closed.

An apparatus for use in indirect bonding of orthodontic appliances according to one embodiment of the invention is broadly designated by the numeral 20 in FIGS. 1 and 2. The apparatus 20 includes a container 22 having a chamber 24. A cover 26 of the container 22 is movable between a closed position as shown in FIG. 2 wherein the cover extends across the chamber 24 and an open position as shown in FIG. 1 wherein the cover 26 is spaced apart from the chamber 24.

In the examples shown in the drawings, the container 22 has a generally "U"-shaped bottom and an upright side wall that defines a generally "U"-shaped configuration in bottom view. A rectangular top flange surrounds an opening to the chamber 24 and is integrally connected to the side wall of the container 22. A pressure sensitive adhesive on the cover 26 engages the top flange for releasably retaining the cover 26 in the closed position. Other constructions are also possible.

An orthodontic placement device 28 is received in the chamber 24. Preferably, the chamber 24 has structure that contacts the placement device 28 so that the latter does not unduly shift when the cover is closed. For example, the sides of the chamber 24 may have a shape complemental to the shape of the placement device 28. Alternatively, bars, posts or other structure could be provided in the chamber 24 to contact the placement device 28 and prevent undue movement.

As an additional option, the chamber 24 may have structure for facilitating gripping of the sides of the placement device 28 so that the placement device 28 can be easily removed from the chamber 24 when desired. For example, sides of the chamber 24 may have recesses for receiving the practitioner's fingers, so that the sides of the placement device 28 can be easily grasped. As another option, the posts or bars mentioned in the previous paragraph could be properly sized and spaced apart from each other in order to enhance gripping of the sides of the placement device 28.

Figure 3:
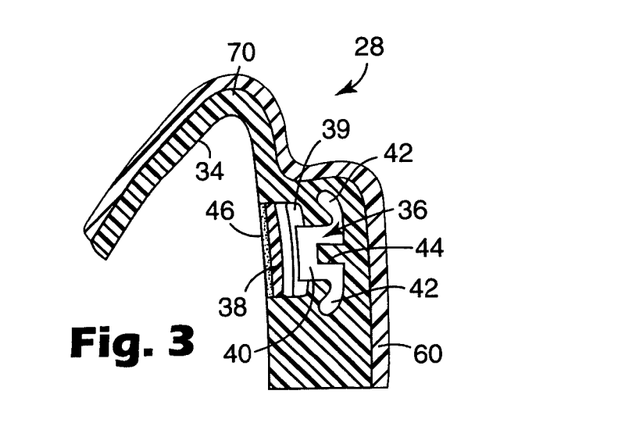
FIG. 3 is an enlarged side cross-sectional view of the placement device alone that is illustrated in FIGS. 1 and 2, additionally showing an orthodontic appliance connected to the placement device.

FIG. 3 depicts the placement device 28 in more detail. As illustrated, the placement device 28 includes an outer shell 60 and a matrix material 70 that is received in the shell 60. The matrix material 70 includes a cavity 34 having a construction that matches a portion of the patient's dental arch.

At least one orthodontic appliance is releasably connected to the placement device 28. Preferably, a number of orthodontic appliances are releasably connected to the placement device 28 such that an appliance is provided for each tooth of the dental arch that is subject to orthodontic treatment. In FIG. 3, an exemplary orthodontic appliance is designated by the numeral 36 and is a bracket, although other appliances such as buccal tubes, buttons and other attachments are also possible.

The appliance 36 includes a base 38 that is connected to a base flange 39. The appliance 36 also has a body 40 that extends outwardly from the flange 39. A pair of tiewings 42 are connected to the body, and an archwire slot 44 extends through a space in the tiewings 42. The base flange 39, the body 40 and tiewings 42 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina) and plastic materials (such as fiber-reinforced polycarbonate). Optionally, the base flange 39, the body 40 and the tiewings 42 are integrally made as a unitary component.

The base 38 of the appliance 36 is preferably made of a material different than the material comprising the base flange 39, and has a configuration that matches the configuration of a portion of a patient's tooth structure. More particularly, the base 38 has a concave contour that is a replica of the convex contour of the portion of the patient's tooth that represents the ultimate desired location of the appliance 36 on the tooth. The concave contour of the base 38 may be a compound concave contour (i.e., curved in directions along two mutually perpendicular reference axes).

A bonding composition 46 extends across the base 38 of each appliance 36. The bonding composition 46 serves in whole or at least in part to securely fix the appliance 36 to the patient's tooth by a bond having sufficient strength to resist unintended detachment from the tooth during the course of treatment. Preferably, the bonding composition 46 is applied by the manufacturer to the base 38 of each appliance 36 before such time as the placement device 28 is placed in the chamber 24.

The bonding composition 46 may be a liquid, a paste or a solid material that is converted into a liquid or paste during the bonding procedure. Suitable compositions include composites, compomers, glass ionomers and resin-modified glass ionomers. Examples of light-curable adhesives include Transbond XT brand and Transbond LR brand adhesives from 3M Unitek. Examples of chemical curing adhesives include Sondhi brand Rapid-Set indirect bonding adhesive, Unite brand adhesive, Concise brand adhesive and Multi-Cure brand glass ionomer cement from 3M Unitek. The bonding composition 46 could be one component of a two-component adhesive such as one component of the chemical curing adhesives described above, wherein the other component is applied by the practitioner to the tooth.

Optionally, the bonding composition 46 is a composition that falls in one of the following classes in accordance with the practitioner's preferences for tooth treatment:

Class I: A bonding composition that requires both etching of tooth enamel (using, for example, phosphoric acid or a bisphosphonic acid) and a separate application of a primer to the tooth enamel.

Class II: A bonding composition that requires etching (using, for example, phosphoric acid, a bisphosphonic acid or self-etching primer) but not a separate application of primer.

Class III: A bonding composition that requires no treatment of the teeth other than cleaning.

Possible tooth primers for use with class I adhesives includes orthodontic primers such as Transbond MIP brand adhesive and Transbond XT adhesive from 3M Unitek and Ortho Solo brand adhesive from Ormco Corporation. Optionally, the primer may include a photobleachable dye to ensure adequate coverage of the primer on the teeth, a small amount of fluoroalumina silicate glass ("FAS" glass) for providing fluoride release during treatment, a small amount of fumed silica for rheology control purposes, and/or a small amount of silanated quartz filler for enhanced fracture toughness. Suitable class I adhesives for the bonding composition 46 include the use of primers described above.

Suitable class II bonding compositions include the adhesives mentioned above. The tooth primer is either absent or replaced by a self-etching primer such as Transbond Plus SEP brand primer from 3M Unitek. Optionally, the self-etching primer could incorporate the optional features described above for the class I adhesive.

Suitable class III bonding adhesives avoid the need for etching and priming the teeth and may be referred to as "self-adhesive" compositions. With these adhesives, the practitioner need only clean the teeth prior to application of the placement device 28 in a typical bonding procedure. Suitable class III adhesives may include an acid component selected from a methacrylate phosphate (e.g., mono-HEMA phosphate, di-HEMA phosphate, glycerol dimethacrylate (GDMA) phosphate), a solution of a bisphosphonic acid in water or other solvent, and a bisphosphonic acid in powder form (using water for ionizing that is left on the teeth after tooth prophy and rinse). Other class III adhesives may include an ethylenically unsaturated component with acid functionality, an ethylenically unsaturated component without acid functionality, an initiator system, and a filler. Optionally a class III adhesive may be essentially free of water. Examples of class III adhesives have been previously described, e.g. in pending U.S. provisional application No. 60/494,603 filed Aug. 12, 2003, which is hereby expressly incorporated by reference herein.

The class III adhesives described above could optionally incorporate a glass ionomer-type filler that binds the water in the usual glass ionomer setting reaction. In addition, any of the class III adhesives described above may incorporate the optional features described in connection with class I adhesives.

The container 22 including the cover 26 is constructed to protect the bonding composition 46 from contaminates such as dust, moisture and the like. In addition, the container 22 including the cover 26 is constructed to avoid deterioration of the adhesive characteristics of the composition 46, so that the ultimate strength of the bond between the appliance 36 and tooth is relatively high. If, for example, the bonding composition 46 is curable upon exposure to actinic radiation, the container 22 is constructed of a material that provides a substantial barrier to the transmission of actinic radiation. Suitable materials for the container 22 include flexible plastic materials such as black or red polyethylene-terephthalate glycol (PETG). Preferably, the container 22 is made of a material that substantially hinders the passage of actinic radiation but enables the passage of light in at least a portion of the visible spectrum so that the presence of the placement device 28 within the container 22 can be confirmed without opening the cover 26. As another option, the cover 26 may include a layer of paper that is bonded to a barrier layer such as aluminum foil. The barrier layer substantially blocks the passage of volatile components of the bonding composition 46. Examples of suitable materials for the container 22 as well as methods for constructing the container 22 are set out in applicant's U.S. Pat. Nos. 5,538,129 and 5,354,199 as well as in applicant's pending U.S. patent application entitled "CONTAINERS FOR PHOTOCURABLE MATERIALS" Ser. No. 10/126,804, filed Apr. 18, 2002, all of which are expressly incorporated by reference herein.

Alternatively, the container 22 may include a hermetic seal in regions between the flange of the container 22 and the cover 26 instead of the pressure sensitive adhesive. The use of a hermetic seal helps to prevent volatile components of the bonding composition 46 from contacting a pressure sensitive adhesive such as the pressure sensitive adhesive on the cover 26 as described above. As a result, the hermetic seal decreases the loss of volatile components from within the chamber 24.

As an additional option, the container 22 may be provided with an additional quantity of one or more components of the bonding composition 46 that are volatile, to help decrease the loss of volatile components that are present in the bonding composition 46 applied to the base 38 of the appliances 36. For example, the bonding composition 46 may contain ethyl 4-dimethylaminobenzoate ("EDMAB") and/or camphorquinone ("CPQ"), both of which may volatilize over a period of time after the container 22 is closed. By adding an additional quantity of such components in the chamber 24, equilibrium is shifted and there is less likelihood of losing an undue quantity of such components from the composition 46 that is applied to the appliances 36. As a result, there is less likelihood that the characteristics of the composition 46 are impaired over a period of time. The additional volatile components may be provided in a liquid that is placed in a well adjoining the chamber 24, or may be placed in a porous material (such as a sponge or fabric) that optionally serves as a packing material for the placement device 28.

Preferably, the container 22 is constructed so that the cover 26 is self-retained in the open position as illustrated in FIG. 1 once the container 22 is opened. To this end, the cover 26 may be provided with a line of weakness such as a series of perforations that extends along an axis that is designated 48 in FIG. 1. In addition to helping retain the cover 26 in an open orientation, the perforations also provide tactile feedback to the user that the cover 26 is open so that the user does not continue to pull on the cover 26 and separate the same from the flange of the container 22.

FIGS. 4–9 illustrate a preferred method of making the placement device 28, although other methods are possible. In the illustrated method, a replica 50 is first made of a portion of a dental arch of an orthodontic patient. For exemplary purposes, the replica 50 represents the patient's lower dental arch. However, a replica of a patient's upper dental arch may be provided as an addition to or as an alternative to the lower dental arch replica as shown. As a further option, the replica 50 may represent only a portion of a dental arch, such as a quadrant of an arch or only one or two teeth of a dental arch. In the example illustrated, the replica 50 includes a number of replica teeth 52, corresponding to each tooth of the patient's lower dental arch.

Figure 4:
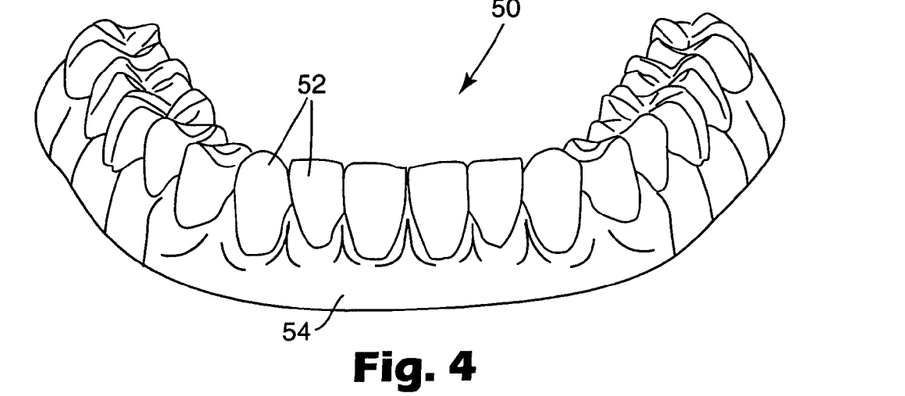
FIG. 4 is a top and front view showing a physical replica of one dental arch of an orthodontic patient, illustrating an example of a replica of a patient's tooth structure and adjacent gingival tissue as they might appear during the commencement of treatment.

Optionally, the replica 50 is made by first taking an impression of the patient's lower dental arch, using care to avoid undue distortion. Optionally, an alginate impression material is used such as Unijel II brand alginate impression material from 3M Unitek. Alternatively, a hydrocolloid or vinyl polysiloxane impression material may also be used, such as Position brand Penta brand vinyl polysiloxane impression material from 3M ESPE.

The model or replica 50 is then made from the impression. Optionally, the replica 50 is a "stone" model made from plaster of Paris, using care to avoid bubbles in the model. If small voids are present, the voids can be filled with a small, additional quantity of plaster of Paris. As an option, the replica 50 includes only the replica teeth 52 and sufficient replica gingival tissue 54 to hold the replica teeth 52 together.

As an alternative, the replica 50 may be made using digital data that is representative of the patient's teeth and adjacent gingival tissue. The digital data may be obtained by use of a hand-held intra-oral scanner or other device known in the art. As another option, the digital data may be obtained by scanning an impression or a stone model. The replica 50 may then be made from the digital data using, for example, a stereo lithographic printer.

The replica 50 may also be made using digital data in conjunction with a milling process. For example, a CNC milling machine, similar to the CAD/CIM milling machines sold by Cerec Network of Buelach, Switzerland, may be used to mill replicas made of ceramic, composite or other materials. An intra-oral camera, similar to the cameras associated with the Cerec machines, may be used to obtain digital data representing the shape of the dental arches. Alternatively, a scanner may be used to scan an impression or a model of an impression to obtain the digital data.

If the orthodontic practitioner takes the impression, the practitioner could send either the impression or the replica to a manufacturer of indirect bonding trays. Alternatively, the practitioner could send a digital data file of scanned teeth. In either instance, the practitioner preferably also sends his or her instructions regarding placement of the appliance on the teeth.

Preferably, the replica 50 is an accurate representation of the patient's oral structure. In particular, the replica teeth 52 will have a configuration and orientation that is identical to the configuration and orientation of the corresponding teeth of the orthodontic patient. In addition, the replica gingival tissue 54 will have a shape that matches the shape of the corresponding portions of the gingival tissue of the patient.

Figure 5:
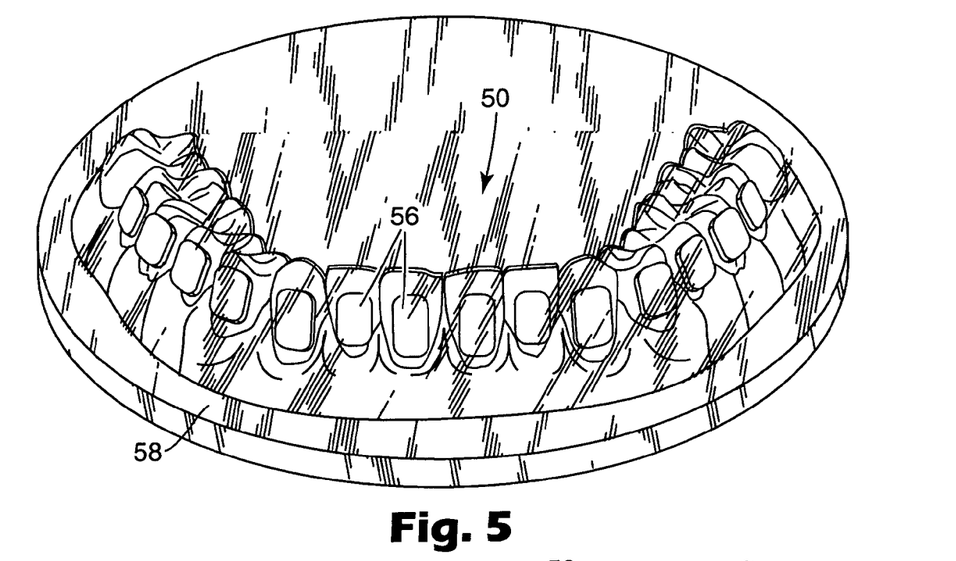
FIG. 5 is a view of the dental arch replica shown in FIG. 4, along with spacer material that has been applied to the replica.
Figure 6:
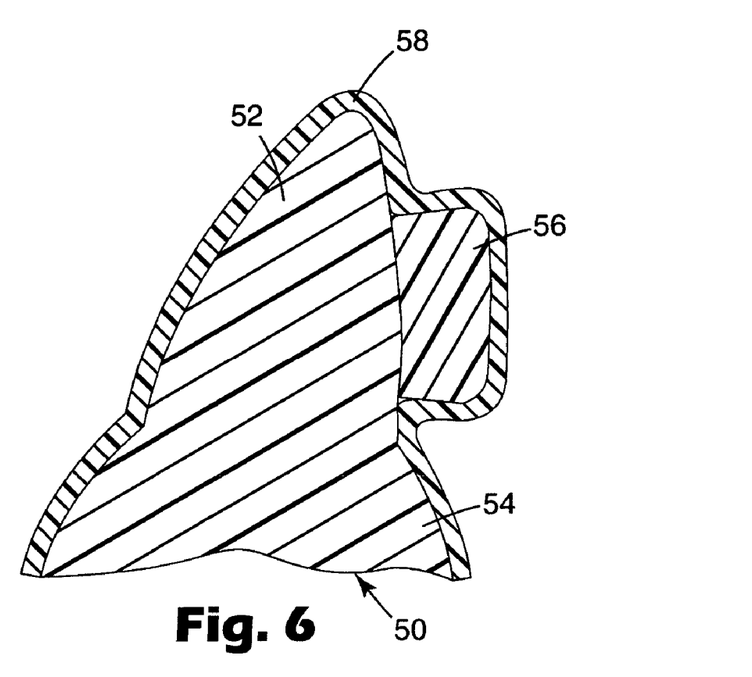
FIG. 6 is an enlarged side cross-sectional view of one of the replica teeth illustrated in FIG. 5 along with the spacer material.

Next, and as shown in FIGS. 5 and 6, a spacer material is applied to the replica 50. In this example, the spacer material includes a first spacer material 56 that comprises a series of discrete dabs or pre-formed segments of material that are placed at approximate, pre-determined locations on the replica teeth 52. Each of the dabs or segments of spacer material 56 is placed in a location that corresponds to a subsequent location of an orthodontic appliance and has an overall size that is at least as large as the selected appliance. For instance, each of the segments of spacer material 56 is placed in a location corresponding to the facial axis point (or "FA" point) of the corresponding tooth, although other locations are also possible. As will be described below, each of the segments of spacer material 56 functions to subsequently provide clearance in the placement device for receiving an orthodontic appliance.

As an alternative to segments of spacer material 56, the spacer material 56 may instead have an elongated configuration in the form of a strip. The strip has sufficient length to extend across at least some, and preferably all, of the replica teeth 52, following a path that corresponds to a subsequent position of an archwire. The strip has sufficient width to provide clearance for each of the appliances that is subsequently affixed to the archwire. In practice, spacer material in the shape of a strip may be preferred in instances where the teeth are initially in general alignment with each other (as the teeth appear in FIG. 1), while the spacer material in the shape of discrete segments or dabs may be preferred in instances where the teeth are substantially crooked and/or out of substantial alignment with each other.

In this embodiment, the spacer material also includes a sheet of spacer material 58 that preferably extends across a substantial portion of the surfaces of the replica teeth 52 and preferably across at least a portion of the surface of the replica gingival tissue 54. As shown in FIG. 6, the sheet spacer material 58 also extends over the segments of spacer material 56. In the illustrated example, the sheet of spacer material 58 extends over the entire buccolabial surface area of the replica teeth 52, along the occlusal edge of the replica teeth 52 and across the entire lingual side of the replica teeth 52, although other constructions are also possible.

As another alternative, the spacer material 56, 58 may be provided as an integral unitary section of material, such that separate handling of the two materials is avoided. Additionally, the sheet of material 58 (whether alone, or whether integral with the spacer material 56) may be preformed to a configuration that approximates the shape of a dental arch. Such construction facilitates subsequent conforming of the sheet 58 to the replica teeth 52 as will be described below.

The spacer material 56, 58 can be any one of a number of materials. A suitable material is a silicone material, such as "RTV 615" from General Electric. Optionally, the spacer material 56 may be temporarily held in place on the replica 50 by use of an adhesive, such as a pressure sensitive adhesive. Optionally, the segments or strips of spacer material 56 may be preformed, coated with a layer of pressure sensitive adhesive on one side and initially connected to a sheet of release material until such time as it is needed for use. Alternatively, dabs of spacer material may be provided by dispensing a quantity of flowable, hardenable material from a syringe and then shaping each dab as needed with a hand instrument.

Next, a vacuum is applied to the replica 50 and the spacer material 56, 58 in order to form the sheet of spacer material 58 to the configuration of the replica teeth 52 and gingival tissue 54. As used herein, the term "vacuum" is not necessarily limited to an absolute vacuum, and shall be understood to mean any pressure that is lower than atmospheric. In practice, the replica 50 along with the spacer material 56 is placed on a disc-shaped support having channels communicating with the vacuum pump. The sheet of spacer material 58 is then placed over the replica and the vacuum pump is activated to draw down the sheet of spacer material 58 into tight, matching conformance with the shape of the replica teeth 52 and gingival tissue 54.

Figure 7:
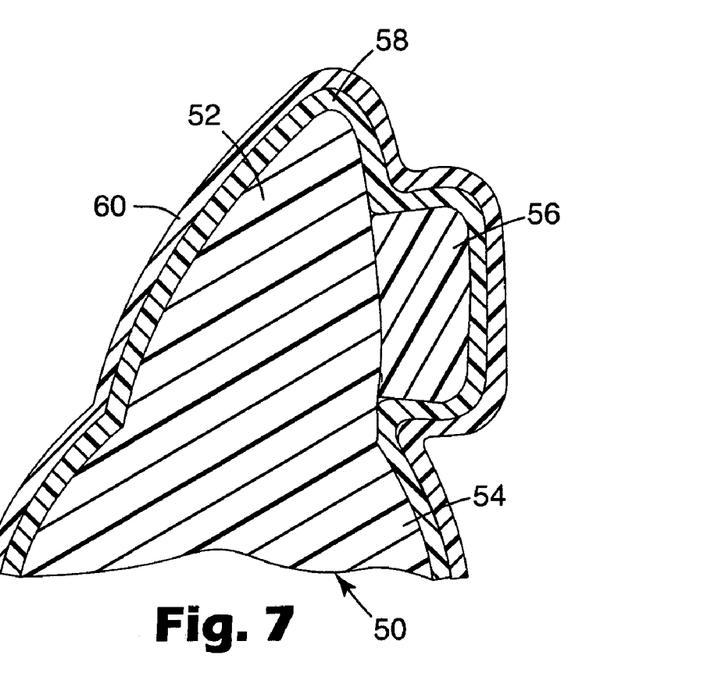
FIG. 7 is a view somewhat similar to FIG. 6, additionally showing a tray that has been formed over the spacer material.

Subsequently, an outer shell 60 is formed over the spacer material 56, 58 as illustrated in FIG. 7. Preferably, the shell 60 is shaped by vacuum forming a sheet of material over the sheet of spacer material 58. A suitable material for the shell 60 is a sheet of polycarbonate such as Makrolon brand material from Bayer or Lexan brand polycarbonate from GE having a thickness of 0.06 inch. Other materials, such as polyethyleneterephthalate glycol ("PETG") may also be used. Heat is applied during the vacuum forming process in order to facilitate conformance of the sheet to the configuration of the sheet of spacer material 58.

Once the shell 60 has hardened, the shell 60 is detached from the spacer material 56, 58. The spacer material 56, 58 is then detached from the replica 50 and set aside. Excess portions of the shell 60 may be trimmed as desired.

A thin layer of a release agent is then applied to the replica 50 and allowed to dry. An example of a suitable release agent is a water soluble polyvinyl alcohol, such as "PA0810" from PTM & W Company of Santa Fe Springs, Calif.

Next, a determination is made of the proper intended position of each appliance on the replica teeth 52, corresponding to the ultimate desired position of the same appliance on the patient's corresponding tooth. A variety of methods are available for determining proper appliance position. For example, the practitioner, practitioner's assistant or lab technician may make a pencil mark across the labial surface of each replica tooth 52. The pencil mark is preferably made with the assistance of a height gauge such as the MBT™ bracket positioning gauge or the Boone bracket positioning gauge, both from 3M Unitek Corporation. The pencil line is drawn across the labial surface of each replica tooth 52 to serve as a location guide for placement of the archwire slot of each orthodontic appliance (such as an orthodontic bracket).

Figure 8:
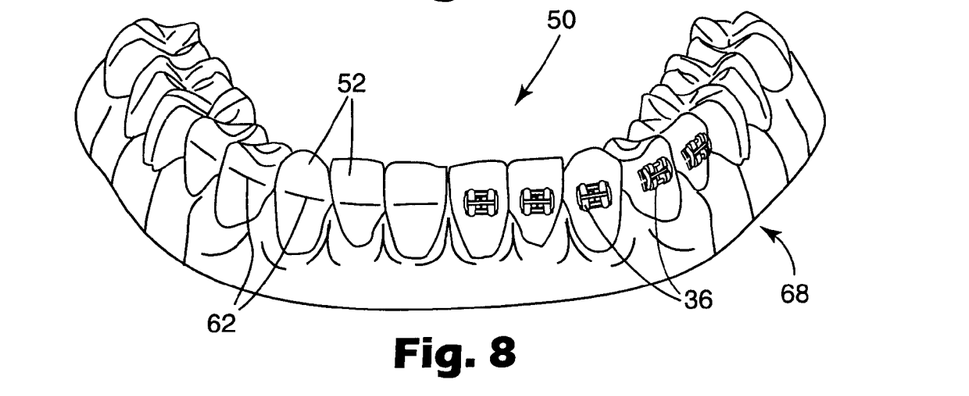
FIG. 8 is a view of the tooth structure replica illustrated in FIG. 4 after the spacer material and the tray have been removed, additionally showing a number of orthodontic appliances that have been placed in predetermined positions on the replica.

For example, and for the replica 50 representing the patient's lower dental arch, pencil lines may be drawn parallel to the occlusal plane according to one treatment technique at a distance of 3.5 mm from the occlusal edge of the replica anterior teeth 52. Similar lines are drawn at a distance of 4.0 mm from the occlusal edge of the replica lower cuspid teeth 52 and the replica lower bicuspid teeth 52. Lines are also drawn parallel to the occlusal plane at a distance of 3.5 mm from the occlusal edge of each replica molar tooth 52 (unless the corresponding tooth of the patient will receive an appliance that is mounted on a band). In FIG. 8, some of the pencil lines as described above are designated by the numeral 62.

Next, orthodontic appliances 36 (such as orthodontic brackets and buccal tubes) as selected by the practitioner are placed on the corresponding replica teeth 52, preferably in positions such that the archwire slot of each appliance 36 is approximately aligned with the respective pencil line 62. Before each appliance 36 is placed on the respective replica tooth 52, a quantity of a composition to make the base 38 is placed between each appliance and the corresponding tooth 52. Preferably, the composition is a light-curable composition such as a light-curable adhesive, and the adhesive is coated across the base of each appliance 36.

Preferably, the appliances 36 are adhesive precoated appliances that have a layer of light-curable adhesive applied to the base flange 39 of each appliance 36 in advance. Such adhesive coated appliances are described in U.S. Pat. Nos. 5,015,180, 5,172,809, 5,354,199 and 5,429,229, all of which are assigned to the assignee of the present invention. The appliances 36 may be made of any suitable material such as metal (e.g., stainless steel), ceramic (e.g., translucent polycrystalline alumina) or plastic (e.g., translucent polycarbonate).

If the appliances 36 are not precoated with adhesive in advance, a coating of adhesive may be applied to the base flange 39 of each appliance 36 immediately prior to placing the appliances 36 on the replica teeth 52. Suitable adhesives include composites, compomers, glass ionomers and resin-modified glass ionomers. Examples of light-curable adhesives include Transbond XT brand or Transbond LR brand adhesives from 3M Unitek. Examples of chemical curing adhesives include Concise brand adhesive and Multi-Cure brand glass ionomer cement from 3M Unitek.

Optionally, the adhesive on the base flange 39 of each appliance 36 may include a color-changing property that facilitates the cleaning of flash (i.e., excess adhesive) along the periphery of the base flange 39 once the appliances 36 are in place. Examples of suitable color-changing adhesives are described in pending U.S. patent application entitled "Orthodontic Adhesive and Appliances Including an Adhesive on the Base of the Appliance", Ser. No. 10/126,505, filed Apr. 18, 2002.

As another option, the adhesive used in the fabrication of the base 38 may include fluoride ions that release during the course of orthodontic treatment. Fluoride may be included in a compomer adhesive or in a glass ionomer adhesive. The release of fluoride in the patient's oral cavity helps reduce the formation of caries, and is especially important with adolescent patients that are not rigorous in maintaining good oral hygiene in the vicinity of the appliances.

Once the appliances 36 have been placed on the replica teeth 52, the appliances 36 are shifted mesial-distally as needed to align the central occlusal-gingival axis of the appliance 36 with the long axis of each replica tooth 52. The appliances 36 are also shifted in an occlusal or gingival direction as needed in order to place the archwire slot of each bracket directly over the underlying pencil line 62. Optionally, a gauge such as the MBT™ gauge or Boone bracket positioning gauge mentioned above is used again to precisely position the archwire slot of each appliance 36 the distance specified above from the occlusal edge of the corresponding replica tooth 52.

Next, firm pressure is applied to each appliance 36 in order to seat each appliance 36 on the respective replica tooth 52 and embed the base flange 39 in the adhesive. For example, a scaler or other hand instrument may be used to apply force to the archwire slot of each appliance 36. A tool such as a dental explorer is then used to remove any adhesive flash that may have been extruded near the periphery of the base flange 39 during seating of the appliance 36.

The use of a light curable adhesive to make the base 38 is advantageous since a lab technician or assistant can carry out the steps described immediately above and then give the replica 50 to a lab supervisor. The supervisor may then make a final check as to the precise placement of each appliance 36 on the corresponding replica tooth 52 before the adhesive has hardened. As one example, a number of replicas 50 may be prepared by the technician and stored in an opaque container such as a black plastic box until reviewed by the supervisor. In this manner, the supervisor can review the placement of the appliances 36 on a number of different replicas 50 at a convenient time without undue or premature curing of the adhesive.

Once the accuracy of the appliance position has been confirmed, the adhesive is allowed to harden and thereby form the base 38. If a light-curable adhesive is used, the replica 50 may be placed in a curing chamber such as Triad 5000 brand visible light curing system from Dentsply. Preferably, the curing chamber is sufficiently large to contain a number of replicas 50 so that the adhesive on a number of replicas 50 can be cured simultaneously. In such a chamber, the light source and the replicas 50 preferably move relative to each other during energization of the light source to facilitate curing of each portion of the adhesive.

If the appliances 36 are made of metal or other opaque material and if a light-curable adhesive is used, it is preferable to expose the replica 50 to the curing light for a relatively long amount of time such as 3 to 5 minutes to ensure that the adhesive has sufficiently hardened. As an alternative to the light curing chambers mentioned above, a hand-held curing unit may be used, such as Ortholux XT brand curing unit from 3M Unitek.

As an additional option, the replica 50 including the replica teeth 52 may be made from a material that transmits actinic radiation. Suitable materials include epoxy resins that are transparent or translucent when hardened. Preferably, the material is optically clear. An example of a suitable epoxy is E-CAST F-82 clear epoxy resin and No. 302 (or UCE-302) hardener, from United Resin Corporation. Other suitable materials include polyesters and urethanes. The use of transparent or translucent materials is advantageous in instances where the appliances 36 are made of opaque materials, since the actinic radiation can be transmitted through the replica 50 for curing portions of the adhesive that are located adjacent the middle of the appliance base. Actinic radiation can include wavelengths in the visible range, ultraviolet range, infrared range or any combination thereof, in accordance with the type of photoinitiator contained in the adhesive.

Alternatively, the appliances 36 may be placed on the replica teeth 52 by means of robotic equipment. For example, the robotic equipment may include a gripping arm that is programmed to pick an appropriate appliance 36 from a set of appliances and place the selected appliance on the appropriate replica tooth 52. The robotic arm then proceeds to grasp another appliance 36 for placement on another replica tooth 52.

Optionally, the path of movement of the robotic arm and the ultimate position of the placed appliance 36 are determined by computer software that has access to digital data representing a virtual model of the replica 50. The software preferably includes subprograms suitable to analyze the existing malocclusion of the patient and select proper appliances for treatment of the particular malocclusion at hand. Optionally, the software enables the supervisor, practitioner, patient or other observer to see on a monitor or other video output a virtual representation of the patient's teeth as they should appear at the conclusion of treatment using the selected appliances placed on certain locations of the teeth.

Preferably, the software includes subprograms for selecting appliances, analyzing malocclusions and/or predicting tooth movement and final positions of the teeth. An example of software for choosing appliances is described in pending U.S. patent application Ser. No. 10/081,220 entitled "Selection of Orthodontic Brackets", the disclosure of which is expressly incorporated by reference herein. Optionally, the software includes subprograms for making custom orthodontic appliances using, for example, a computer numerical control milling machine, instead of selecting appliances from an existing set of appliances as mentioned above.

As an additional option, an orthodontic archwire may be placed in the slots of the appliances 36 and ligated in place. This step serves to further reduce the patient's time that is subsequently spent in the chair since the step of ligation in the practitioner's office is avoided.

Figures 9, 10:
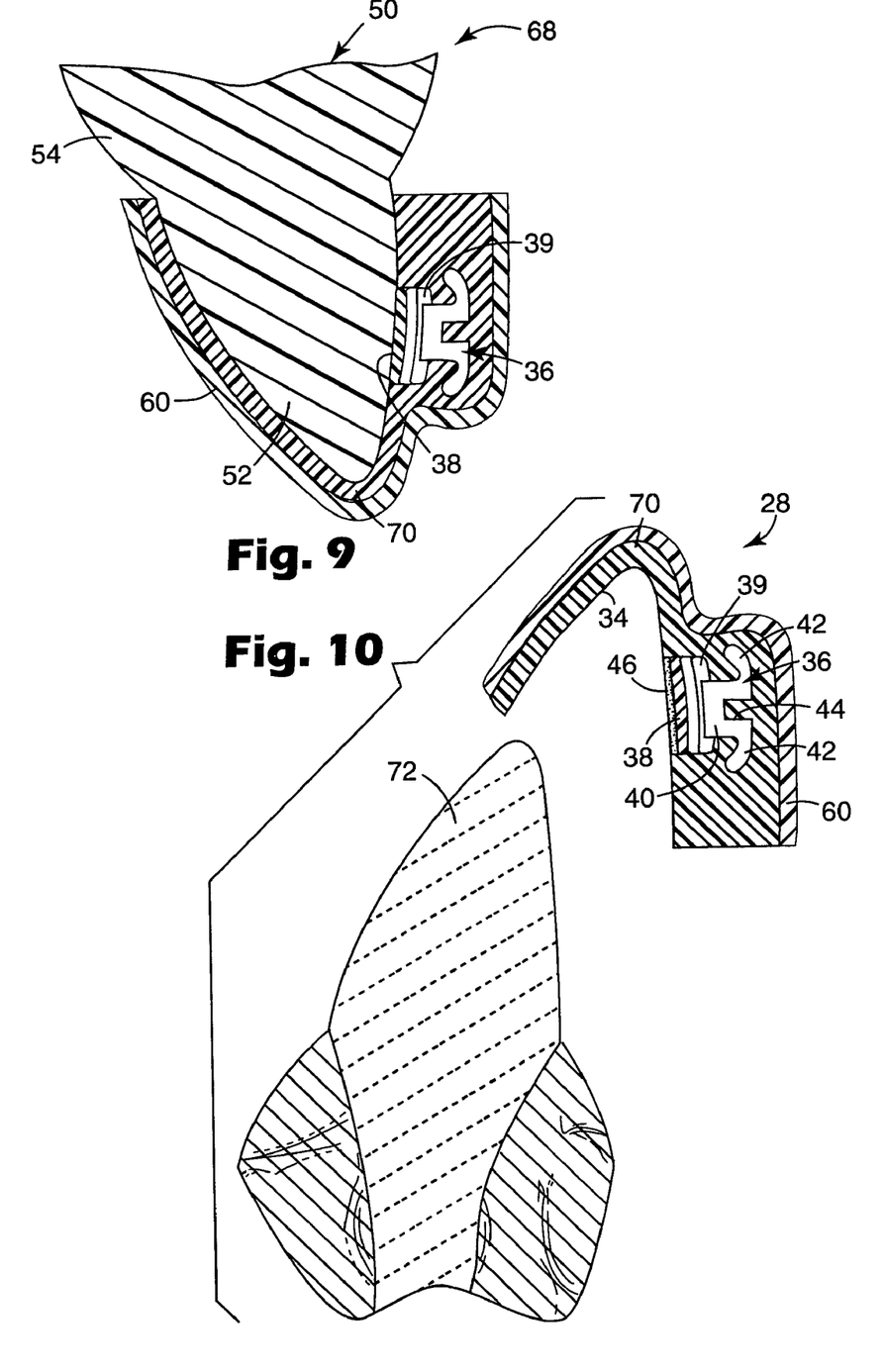
FIG. 9 is an enlarged side cross-sectional view of one of the replica teeth and appliances depicted in FIG. 8, and additionally showing a quantity of matrix material which has been placed between the replica and the tray illustrated in FIG. 7 after the replica and the tray have been inverted to make a placement device.
FIG. 10 is an enlarged side cross-sectional view showing the act of applying the placement device to one of the patient's teeth.

The replica 50, together with the appliances 36 (and the archwire, if any), represent a treatment model 68 of an orthodontic patient set-up as shown in part in FIG. 8. A matrix material is then applied, either to the model 68 or to the channel of the shell 60. For example, if the matrix material is relatively viscous and resembles a semi-liquid or gel, the matrix material may be applied to the model 68 as it appears in FIG. 8, using a syringe, brush or other technique. Alternatively, if the matrix material has a relatively low viscosity and resembles a liquid, it may be preferable to invert the shell 60 such that the open side of the channel of the shell 60 is facing upwardly as shown in FIG. 9. If the shell 60 is inverted, the shell 60 is not initially trimmed along the outermost distal sides (corresponding to the ends of the dental arch) so that the liquid matrix material is contained within the shell channel.

Subsequently, the model 68 is positioned in the shell 60 such that the matrix material is received in the channel of the shell 60 and between the shell 60 and the model 68. In FIG. 9, the matrix material is designated by the numeral 70 and surrounds the appliance 36 as well as the labial and lingual surfaces of the replica tooth 52. The matrix material 70 is then allowed to harden.

Preferably, the matrix material has a relatively low viscosity before hardening so that intimate contact between the matrix material 70 and the appliance 36 is assured. In this manner, the matrix material 70 is able to substantially penetrate in various recesses, cavities and other structural features of the appliance 36 so that a secure connection between the appliance 36 and the matrix material 70 is established. An example of a suitable matrix material having a relatively low viscosity is a silicone material such as "RTV 615" silicone material from General Electric as mentioned above. The relatively low viscosity of this silicone matrix material also assures that the matrix material will assume a configuration that closely matches the shape of the adjacent surfaces of the replica teeth 52.

Alternatively, the matrix material 70 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. If a light-curable adhesive is to be used for bonding the appliances 36 to the patient's teeth, the matrix material 70 is preferably optically clear and transmits actinic radiation without substantial absorption.

Once the matrix material 70 has hardened, the shell 60, together with the matrix material 70 and the appliances 36, are detached from the replica 50. The use of the release agent as mentioned above helps facilitate detaching of the appliances 36 from the corresponding replica teeth 52. Excess material of the shell 60 and excess matrix material 70 are then trimmed as desired and discarded. The resultant trimmed placement device 28 (comprising the shell 60, the matrix material 70 and the appliances 36) is shown in cross-sectional view in FIG. 10.

Next, the appliances 36 are coated with the bonding composition 46. The placement device 28 is then placed in the chamber 24 of the container 22 by the manufacturer. Subsequently, the cover 26 is applied to the top flange of the container 22 in order to seal the placement device 28 within the chamber 24. The apparatus 20, comprising the container 22 with the placement device 28, is then shipped to the practitioner's office.

Once the patient has returned to the office, bonding procedure is undertaken. The steps of the bonding procedure are determined in part by the particular bonding composition selected by the practitioner. For example, if a class II adhesive is selected, the patient's teeth that are to receive appliances 36 are isolated using cheek retractors, tongue guards, cotton rolls, dry angles and/or other articles as needed. The teeth are then thoroughly dried using pressurized air from an air syringe. Etching solution (such as 3M Unitek Transbond XT brand etching gel) is then dabbed onto the teeth in the general area that is to be covered by the appliances 36, taking care to prevent the etching solution from flowing into interproximal contacts or engaging the skin or gingiva.

After the etching solution has remained on the selected tooth surfaces for a period of approximately 30 seconds, the solution is rinsed away from the teeth with a stream of water for 15 seconds. The patient's teeth are then dried by the application of pressurized air from an air syringe (for example, for a time period of 30 seconds) and excess water is removed by suction. Care should also be undertaken to ensure that the saliva does not come in contact with the etched enamel surfaces. Cotton rolls and other absorbent devices are replaced as needed, again making sure that saliva does not contact the etched enamel. Air from the air syringe may then be applied to the teeth again to ensure that the teeth are thoroughly dried.

Preferably, the tooth preparation steps as mentioned above are carried out before the container 22 is opened. In this manner, the bonding composition 46 is not unduly exposed to ambient light or air. After the tooth preparation steps are completed, the cover 26 of the container 22 is opened as shown in FIG. 1 and the placement device 28 is lifted from the chamber 24.

The shell 60 is then positioned over the corresponding teeth and seated, optionally with a swinging, hinge-type motion. In FIG. 10, the patient's tooth is designated by the numeral 72. Since the shape of the cavity of the matrix material 70 matches the shape of the underlying teeth, the appliances 36 are simultaneously seated against the underlying teeth 72 at precisely the same locations corresponding to the previous position of the appliances 36 on the replica 50. Preferably, pressure is then applied to the occlusal, labial and buccal surfaces of the shell 60 until such time as the bonding composition 46 has sufficiently hardened. Optionally, finger pressure may be used to firmly press the appliances 36 against the enamel surfaces of the patient's teeth 72.

Once the bonding composition 46 has hardened, the shell 60 is carefully removed from the patient's dental arch. Preferably, the shell 60 is first separated from the matrix material 70, which remains in place over the dental arch along with the appliances 36. Next, the matrix material 70 is detached from the appliances 36. Optionally, a hand instrument such as a scaler may be used to help hold each appliance 36 against the surface of the respective tooth 72 of the patient as the matrix material 70 is peeled away from the appliances 36. However, in instances where a relatively soft matrix material is employed or otherwise readily releases from the appliances 36, the use of a scaler to help avoid fracturing the fresh adhesive bond is optional.

As another option, the shell 60 may be separated from the matrix material 70 before the bonding composition 46 has hardened. This option is particularly useful when the bonding composition 46 is a light-curable adhesive.

Once the matrix material 70 has been detached from the appliances 36, an archwire is placed in the slots of the appliances 36 and ligated in place. Suitable ligation devices include tiny, elastic O-rings as well as sections of wire that are tied in a loop around the appliances 36. As another option, the appliances 36 may be self-ligating appliances that include a latch for releasably engaging the archwire such as those described in U.S. Pat. No. 6,302,688 and PCT Publication No. W002/089693.

The use of the spacer material 56, 58 in the method described above is a significant advantage in that an appropriate region for receiving matrix material 70 in the shell 60 is provided. The spacer material 56, 58 can be shaped as needed to provide precisely the volume and configuration of region as may be desired. For example, the sheet of spacer material 58 ensures that a uniform thickness of matrix material is subsequently provided around the substantial extent of the tooth 72 with the exception of the areas adjacent the appliance 36.

Moreover, the use of the spacer material 56, 58 facilitates the use of a matrix material having a relatively low viscosity, such as a matrix material having a liquid consistency. The shell 60 is relatively stiff, and consequently maintains its shape during forming of the matrix material 70. As a result, the placement device 28 is constructed such that the shell 60 does not directly contact the patient's teeth or gingival tissue. Instead, only the matrix material 70 comes into contact with the patient's teeth, so that a close, matching fit with such oral structure is provided.

Advantageously, the relatively soft matrix material 70 is flexible and can accommodate a limited amount of tooth movement. For example, the teeth of the patient may have slightly shifted between the time that the impressions are taken and the time that the placement device 28 is fitted in the patient's oral cavity for bonding the appliances 36. The matrix material 70 has sufficient flexibility to comply with small shifts or adjustments in the patient's tooth positions, so that the appliances 36 are properly bonded to the intended, pre-determined locations on the patient's tooth.

The matrix material 70 preferably has a viscosity before curing that is less than about 60,000 cp. More preferably, the matrix material 70 has a viscosity before curing that is less than about 25,000 cp. Most preferably, the matrix material 70 has a viscosity before curing that is less than about 8000 cp. Once hardened, the matrix material 70 has a Shore A hardness that is in the range of about 10 to about 80, more preferably in the range of about 30 to about 60 and most preferably in the range of about 40 to about 50. Preferably, the matrix material 70 has a Shore A hardness that is less than the Shore A hardness of the shell 60.

Furthermore, the use of the spacer material 56, 58 enhances control over construction of the placement device, including the resultant shape of the shell 60 and the contained matrix material 70. For instance, the sheet of spacer material 58 enables the resultant thickness of the matrix material 70 to be relatively uniform and preferably relatively thin. This uniform thickness of relatively small dimension facilitates curing of a photocurable adhesive when used as the bonding composition 46. Specifically, when a light-curable composition is used to bond the appliances 36 to the patient's teeth, the uniform thickness of matrix material 70 helps to ensure that the composition 46 beneath each appliance 36 is sufficiently cured to the same extent from one appliance 36 to the next. In this manner, the user need not compensate for varying thicknesses of matrix material and the curing times associated with each quantity of adhesive need not vary from one appliance 36 to the next.

As an alternative to the use of a physical replica as described above, another method of making the apparatus 20 of the present invention involves the use of a milling machine or other device to form the contour of the base 38 using a digital model of the patient's tooth structure. The digital model of the patient's tooth structure may be obtained by the use of a hand-held intra-oral scanner or other device known in the art. Alternatively, the digital data may be obtained by scanning an impression of the patient's tooth structure or a physical model (such as a stone model) made from an impression of the patient's tooth structure.

The base 38 may then be made using the digital data in conjunction with a manufacturing process such as a milling process. For example, a CNC milling machine may be used with the digital data to provide a contour on the base 38 that precisely replicates the contour of the tooth structure of interest.

Suitable examples of material for the base 38 include the compomers, composites and glass ionomer materials described above. Preferably, the base 38 is made of a translucent material or tooth-colored material, particularly in instances where the appliance body 40 is also made of a translucent material or tooth-colored material.

A variety of other alternatives are also possible and will be apparent to those skilled in the art. For example, various aspects of the transfer apparatus described in the aforementioned pending U.S. patent application Ser. No. 10/428,301 filed May 2, 2003 (which is expressly incorporated by reference herein) may be used in the placement device 28 of the present invention.

Additionally, the placement device 28 may be used for bonding only a single appliance to a patient's tooth. For example, a portion of the placement device 28 described above may be used to bond a single appliance to a single tooth, such as in instances where access to the tooth is initially hindered by other teeth. A portion of the placement device 28 described above may also be used to rebond an appliance that has unintentionally debonded from the tooth, or to bond a new appliance to a tooth to replace an original appliance. The placement device 28 may also be constructed to extend along a quadrant of a dental arch, instead of the full arch as illustrated in the drawings.

Figure 11:
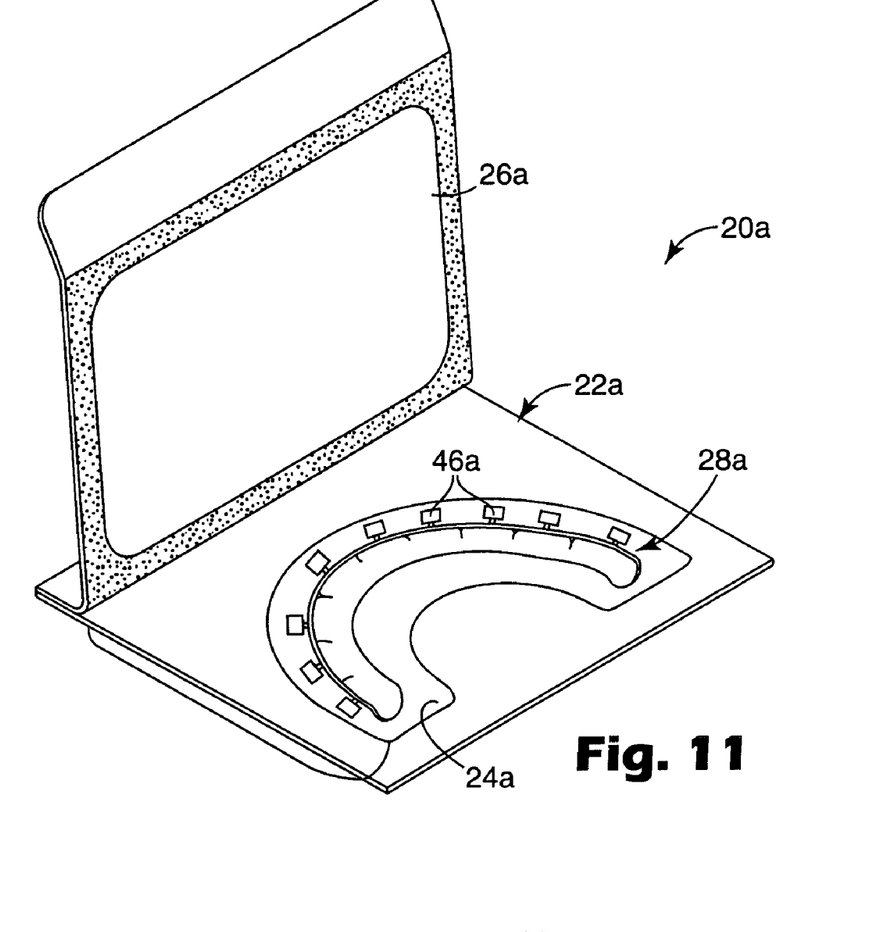
FIG. 11 is a perspective view showing an apparatus for use in indirect bonding of orthodontic appliances according to another embodiment of the present invention.
Figure 12:
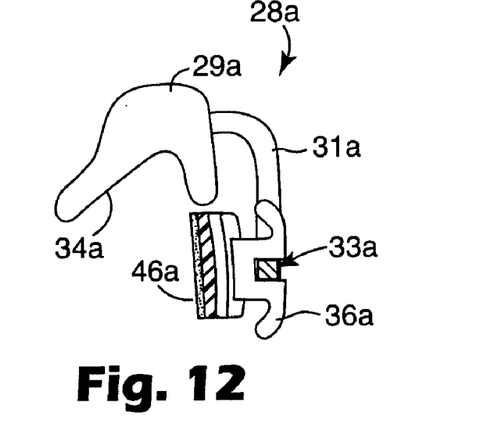
FIG. 12 is a side cross-sectional view of a placement device alone of the apparatus of FIG. 11.

An apparatus for indirect bonding of orthodontic appliances according to another embodiment of the invention is illustrated in FIGS. 11 and 12 and is designated by the numeral 20a. The apparatus 20a includes a container 22a having a chamber 24a. A cover 26a of the container 22a is similar in function to the cover 26 described above.

An orthodontic placement device 28a comprising a jig is removably received in the chamber 24a. A side cross-sectional view of the placement device 28a alone is depicted in FIG. 12, and includes a body 29a having a cavity 34a with a configuration that matches a portion of the patient's dental arch. In the illustrated embodiment, the cavity 34a matches the configuration of an occlusal section of each tooth of one of the patient's dental arches.

Preferably, the body 29a is made of a soft material such as cured silicone impression material. Examples of suitable impression materials include "Express STD" brand impression material from 3M Espe and other polyvinylsiloxane impression materials commercially available. The "RTV 615" silicone from General Electric may also be employed.

The placement device 28a also includes an arm 31a having a generally "L"-shaped configuration. One side of the arm 31a is embedded in the body 29a and the other side of the arm 31a is releasably connected to an orthodontic appliance 36a. Optionally, the arm 31a is made of an inexpensive plastic material such as polycarbonate.

The releasable connection between the arm 31a and the appliance 36a may comprise any suitable coupling means in accordance with the configuration or type of appliance. In the example shown, the arm 31a extends along a vertical channel between spaced apart tiewings of the appliance 36a. The arm 31a also includes a crosspiece 33a that is releasably received in an archwire slot of the appliance 36a. The arm 31a is constructed so that the appliance 36a remains coupled to the arm 31a by friction until the bonding procedure has been completed.

Other types of releasable couplings are also possible. For example, the arm 31a may include an elastomeric member that snugly extends around the tiewings of the appliance 36a, and remains engaged with the appliance 36a until such time as the bonding procedure is complete. As another option, an adhesive is provided to detachably couple the arm 31a to the appliance 36a.

The appliance 36a is similar to the appliance 36. Additionally, a bonding composition 46a is similar to the bonding compositions 46 and extends across a base flange of the appliance 36a.

In use of the placement device 28a, the body 29a is placed over the occlusal sections of the teeth of the selected dental arch. The arms 31a are constructed to engage the teeth at the proper pre-selected bonding locations as soon as the body 29a is seated in place. However, if desired, finger pressure may be applied to the arms 31a in order to ensure that the base of the appliance 36a is in close contact with the enamel surface of the patient's teeth.

Once the bonding composition 46a has hardened, the placement device 28a is removed from the patient's oral cavity by disengaging the body 29a from the occlusal sections of the teeth. At that time, the arms 31a detach from their respective appliances 36a, such that the latter remain in place firmly bonded to the teeth.

As another alternative, a placement device somewhat similar to the placement device 28a may be provided for only a single tooth, a quadrant of a dental arch, or any other number of teeth of the selected dental arch. For example, the placement device may be adapted for use with a single tooth and placed in a separate container. In that instance, the body of the placement device (corresponding to the body 29a) has a shape that matches the occlusal section of only a single tooth.

As another option, the placement devices 28 and 28a may be used for bonding appliances such as brackets, buccal tubes, bite planes or openers, buttons and lingual sheaths to the lingual surfaces of the patient's teeth. In that instance, the method and materials as described above are adapted and modified as needed.

The apparatus 20, 20a of the present invention is adapted for use with a particular patient. Consequently, as soon as the apparatus 20, 20a has been manufactured, it may be shipped to the practitioner's office and used in a bonding procedure as soon as the patient returns to the practitioner's office. Often, there is no need for undue delay between the time that the apparatus 20, 20a is manufactured and the time that the placement device 28, 28a is used to bond appliance to the patient's dental arches.

Accordingly, a wide variety of compositions are available for use as the bonding composition 46 described. Since the apparatus may be manufactured and arrive in the practitioner's office in a matter of days, the problems normally associated with shelf life of adhesives are significantly diminished. Such construction is an advantage over packaged, precoated orthodontic appliances having "standard" bases as described in the references set out above because such appliances are often not adapted for a particular patient and instead may reside in inventory in the manufacturer's plant or in the practitioner's office until such time as is needed for use. For example, bonding compositions that are relatively volatile and may not remain "fresh" for many months may be successfully used with the present invention.

Another advantage of the present invention is that the indirect bonding apparatus requires only a relatively short working time in comparison to direct bonding techniques. As a result, the amount of curatives in the bonding composition 46 may be higher than those typically found in adhesives used in direct bonding applications. Such higher curative levels would also help compensate for the loss of actinic radiation that occurs during passage through the shell 60 and matrix material 70 described above.

A number of other variations, modifications and additions are also possible without departing from the spirit of the invention. Accordingly, the invention should not be deemed limited to the specific embodiments described above, but instead only by a fair scope of the claims that follow and their equivalents.

The invention claimed is:

1. Apparatus for use in indirect bonding of orthodontic appliances comprising:
    a container having a chamber, said container including a barrier layer to reduce the passage of volatile components therethrough;
    an orthodontic placement device received in the chamber, wherein the placement device comprises a tray and has a construction matching at least a portion of the patient's dental arch;
    a plurality of orthodontic appliances releasably connected to the placement device, each appliance having a base with a contour that is a replica of a contour of a portion of the patient's tooth structure; and
    a bonding composition on the base of each appliance for bonding to the patient's tooth structure.

2. The apparatus of claim 1 wherein the tray comprises a shell and a matrix material received in the shell, wherein the matrix material has a Shore A hardness that is less than the Shore A hardness of the shell.

3. The apparatus of claim 1 wherein the placement device extends across all of the teeth of a dental arch.

4. The apparatus of claim 1 wherein the placement device extends across the teeth of a quadrant of a dental arch.

5. The apparatus of claim 1 wherein the base is made of a curable composition.

6. The apparatus of 5 wherein the curable composition is a light-curable composition.

7. The apparatus of claim 1 wherein the container is made of a material that substantially blocks the passage of actinic radiation.

8. The apparatus of claim 1 wherein the container includes structure for substantially hindering shifting of the placement device in the chamber.

9. The apparatus of claim 1 wherein the chamber has a configuration substantially matching the configuration of the placement device.

10. The apparatus of claim 1 wherein the bonding composition comprises a light-curable composition.

11. The apparatus of claim 1 wherein the bonding composition comprises a chemical curing composition.

12. The apparatus of claim 1 wherein the bonding composition comprises one component of a two-component adhesive.

13. The apparatus of claim 1 wherein the container also includes an additional quantity of at least one volatile component of the bonding composition in a location other than in the bonding composition that is applied to the base of each appliance.

14. A method of making apparatus for orthodontic indirect bonding comprising:
    providing a plurality of orthodontic appliances;
    obtaining information in an orthodontic practitioner's office relating to the contour of at least a portion of the patient's tooth structure;
    providing the information to a manufacturer of indirect bonding trays;
    forming a base at the manufacturer's facility on each appliance to replicate a portion of the patient's tooth structure;
    connecting each appliance to a placement device, wherein the placement device comprises an indirect bonding tray;
    applying at the manufacturer's facility a quantity of bonding composition to each base;
    placing the placement device within a container; and
    sending the container to an orthodontic practitioner after the placement device is placed within the container.

15. The method of claim 14 wherein the act of determining the contour of at least a portion of the patient's tooth structure is carried out using digital data.

16. A method of making apparatus for orthodontic indirect bonding according to claim 14 wherein the act of determining the contour of at least a portion of the patient's tooth structure is carried out by taking an impression of the patient's tooth structure.

17. A method of making apparatus for orthodontic indirect bonding according to claim 16 and including the act of making a physical replica using the impression.

18. A method of making apparatus for orthodontic indirect bonding according to claim 14 wherein the base is made of a curable composition.

19. A method of making apparatus for orthodontic indirect bonding according to claim 14 wherein the act of placing the placement device within a container includes the act of placing the placement device in a chamber of the container that is protected from actinic radiation.

* * * * *